United States Patent

Vincent (10) Patent No.: US 9,593,056 B2
(45) Date of Patent: Mar. 14, 2017

(54) PROCESS FOR PRODUCING CUMENE WITH ALKYLATION EFFLUENT RECYCLE

(71) Applicant: ExxonMobil Chemical Patents Inc., Baytown, TX (US)

(72) Inventor: Matthew J. Vincent, Kingwood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 2 days.

(21) Appl. No.: 14/647,238

(22) PCT Filed: Nov. 26, 2013

(86) PCT No.: PCT/US2013/071984
§ 371 (c)(1),
(2) Date: May 26, 2015

(87) PCT Pub. No.: WO2014/093018
PCT Pub. Date: Jun. 19, 2014

(65) Prior Publication Data
US 2015/0315096 A1 Nov. 5, 2015

Related U.S. Application Data

(60) Provisional application No. 61/735,768, filed on Dec. 11, 2012, provisional application No. 61/735,774, (Continued)

(30) Foreign Application Priority Data

Feb. 4, 2013 (EP) ..................................... 13153830

(51) Int. Cl.
*C07C 2/66* (2006.01)
*C07C 1/22* (2006.01)
(Continued)

(52) U.S. Cl.
CPC .............. *C07C 2/864* (2013.01); *C07C 1/22* (2013.01); *C07C 2/66* (2013.01); *C07C 2/867* (2013.01); *C07C 29/143* (2013.01)

(58) Field of Classification Search
CPC .............. C07C 2/66; C07C 1/22; C07C 1/24
(Continued)

(56) References Cited

U.S. PATENT DOCUMENTS 2,909,574 A * 10/1959 Woodle .................... C07C 2/70
208/2
4,185,040 A 1/1980 Ward et al.
(Continued)

FOREIGN PATENT DOCUMENTS

CN 101417915 A 4/2009
CN 101605874 A 12/2009
(Continued)

*Primary Examiner* — Thuan D Dang
(74) *Attorney, Agent, or Firm* — Darryl M. Tyus (57) ABSTRACT

In a process for producing cumene, a $C_3$ feed stream is contacted with an aromatic stream comprising benzene to produce an alkylation effluent comprising cumene. A portion of the alkylation effluent and at least one three-carbon alkylating agent is supplied to a treatment zone to remove impurities to form a treated feedstock. The $C_3$ feed stream comprises a portion of the treated feedstock.

17 Claims, 2 Drawing Sheets

Related U.S. Application Data filed on Dec. 11, 2012, provisional application No. 61/735,765, filed on Dec. 11, 2012.

(51) Int. Cl.
*C07C 1/24* (2006.01)
*C07C 2/86* (2006.01)
*C07C 29/143* (2006.01)

(58) Field of Classification Search
USPC .......................... 585/467, 447, 448, 323, 638
See application file for complete search history.

(56) References Cited

U.S. PATENT DOCUMENTS

| | | |
|---|---|---|
| 4,992,606 A | 2/1991 | Kushnerick et al. |
| 5,015,786 A | 5/1991 | Araki et al. |
| 5,017,729 A * | 5/1991 | Fukuhara ................ C07C 1/24 |
| | | 568/385 |
| 5,073,653 A | 12/1991 | Butler |
| 6,617,482 B1 | 9/2003 | Venkat et al. |
| 6,753,452 B2 | 6/2004 | Venkat et al. |
| 2004/0111001 A1* | 6/2004 | Dandekar ................ C07C 2/66 |
| | | 585/467 |
| 2005/0250971 A1 | 11/2005 | Weber et al. |
| 2010/0298617 A1 | 11/2010 | Clark et al. |
| 2011/0245558 A1 | 10/2011 | Schmidt |

FOREIGN PATENT DOCUMENTS

| | | |
|---|---|---|
| EP | 0 371 738 | 6/1990 |
| EP | 1 069 099 | 1/2001 |
| WO | 03/006405 | 1/2003 |
| WO | 03/053892 | 7/2003 |
| WO | 2008/147634 | 12/2008 |
| WO | 2009/058527 | 5/2009 |
| WO | 2010/029405 | 3/2010 |
| WO | 2010/042315 | 4/2010 |
| WO | 2010/060981 | 6/2010 |
| WO | 2011/161523 | 12/2011 |
| WO | 2012/175614 | 12/2012 |
| WO | 2014/008268 | 1/2014 |
| WO | 2014/011359 | 1/2014 |

* cited by examiner

PROCESS FOR PRODUCING CUMENE WITH ALKYLATION EFFLUENT RECYCLE

CROSS REFERENCE TO RELATED APPLICATIONS

This application is a National Stage Application of International Application No. PCT/US2013/071984, filed Nov. 26, 2013, and claims the benefits of and priorities to U.S. Provisional Patent Application No. 61/735,768, filed Dec. 11, 2012, U.S. Provisional Patent Application No. 61/735,774, filed Dec. 11, 2012, and U.S. Provisional Patent Application No. 61/735,765, filed Dec. 11, 2012, and claims priority to EP 13153830.8, filed Feb. 4, 2013, the disclosures of which are incorporated herein by reference in their entireties.

FIELD

This invention relates to a process for producing cumene by contacting a $C_3$ feed stream with an aromatic stream comprising benzene to produce an alkylation effluent comprising cumene. A portion of the alkylation effluent and at least one three-carbon alkylating agent is supplied to a treatment zone to remove impurities to form a treated feedstock. The $C_3$ feed stream comprises a portion of the treated feedstock.

BACKGROUND

Cumene is an important intermediate in the chemical and polymer industries, with global cumene production currently exceeding twelve million metric tons annually. Cumene is generally produced by the alkylation of benzene with a $C_3$ feed stream (e.g., a $C_3$ alkylating agent) in the presence of an acid catalyst. Early cumene plants used solid phosphoric acid as the catalyst, but more recently most cumene manufacturers have replaced the phosphoric acid with molecular sieve catalysts. Examples of benzene alkylation processes employing molecular sieve catalysts can be found in, for example, U.S. Pat. Nos. 4,185,040; 4,992,606; and 5,073,653.

Most cumene plants operating today employ propylene as the $C_3$ alkylating agent. However, the increasing cost and scarcity of propylene provides a significant incentive to find alternative $C_3$ alkylating agents. In view of a continuing over-supply of acetone, there has for some time been interest in developing a process for using the excess acetone as a feedstock for producing cumene. For example, European Patent No. 1069099 B1 discloses a process for producing cumene by alkylation of benzene with isopropanol, either alone or in admixture with propylene, in the presence of zeolite beta and under temperature and pressure conditions such that the reaction mixture is completely in the gas phase. The isopropanol is produced by hydrogenation of the acetone coproduced when the cumene is converted to phenol.

Commercial processes for the production of cumene using molecular sieve catalysts can be conducted in either the vapor phase or the liquid phase. However, in view of the improved selectivity and decreased capital and operating costs associated with liquid phase operation, most commercial cumene processes now operate under at least partial liquid phase conditions. Unfortunately, one disadvantage of operating under liquid phase conditions is that the molecular sieve catalysts tend to be more sensitive to the presence of impurities in the feedstocks, particularly polar compounds such as nitrogen compounds. Such impurities reduce the acid activity of the catalyst and hence decrease the cycle time between required regenerations of the catalyst. Although important with conventional processes employing propylene as the only $C_3$ alkylating agent, impurities are particularly challenging with processes using oxygenated propyl compounds, such as acetone and isopropanol, as the $C_3$ alkylating agent, or part of the $C_3$ alkylating agent. This is partly because of the molecular polarity of the acetone and isopropanol, which competes with the adsorption of the polar nitrogen compounds, and partly because acetone and isopropanol are reactive even at room temperature for the formation of higher molecular weight oxygenates.

Thus, development of a viable process for the removal of contaminants from a $C_3$ feed stream containing oxygenated propyl compounds (either alone or admixed with propylene) is contingent upon finding an adsorbent material and conditions that allow selective contaminant reduction without excessive conversion of the oxygenated propyl compounds (and/or propylene) to unwanted by-products. The present invention seeks to provide such a process.

SUMMARY

The process comprising the steps of:
(a) contacting a $C_3$ feed stream with an aromatic stream comprising benzene under alkylation conditions effective to produce an alkylation effluent comprising at least 1.0 wt. % of cumene based on the total weight of the alkylation effluent;
(b) supplying a portion of said alkylation effluent and an alkylating feedstock having at least one three-carbon alkylating agent to a treatment zone under treatment conditions to form a treated feedstock; and
wherein said $C_3$ feed stream comprises at least a portion of said treated feedstock.

In another aspect, the invention resides in a process for producing cumene, the process comprising the steps of:
(a) contacting a $C_3$ feed stream with benzene in the presence of an alkylation catalyst under alkylation conditions effective to produce an alkylation effluent comprising at least 1.0 wt. % of cumene based on the total weight of the alkylation effluent;
(b) supplying a portion of said alkylation effluent and an alkylating feedstock having at least one three-carbon alkylating agent to a treatment zone comprising a treatment agent under treatment conditions to form a treated feedstock, said three-carbon alkylating agent comprises one or more of propylene or an oxygenated propyl compound, said oxygenated propyl compound comprises one or more of isopropyl alcohol, or n-propyl alcohol, said treatment conditions in step (b) are selected such that the ratio of the total weight amount of said at least one three-carbon alkylating agent in said alkylating feedstock over the total weight amount of said at least one three-carbon alkylating agent in said treated feedstock is greater than 0.99; and
wherein said $C_3$ feed stream comprises at least a portion of said treated feedstock.

In another aspect, the invention resides in a process for producing cumene, the process comprising the steps of:
(a) contacting a $C_3$ feed stream with benzene in the presence of an alkylation catalyst under alkylation conditions effective to produce an alkylation effluent comprising at least 1.0 wt. % of cumene based on the total weight of the alkylation effluent;

(b) supplying a portion of said alkylation effluent and at least one three-carbon alkylating agent to a treatment zone comprising a treatment agent under treatment conditions to form a treated feedstock, said three-carbon alkylating agent comprises one or more of propylene or an oxygenated propyl compound, said oxygenated propyl compound comprises one or more of isopropyl alcohol or n-propyl alcohol, said treatment conditions in step (b) are selected such that the ratio of the total weight amount of said at least one three-carbon alkylating agent in said alkylating feedstock over the total weight amount of said at least one three-carbon alkylating agent in said treated feedstock is less than 0.99; and wherein said $C_3$ feed stream comprises at least a portion of said treated feedstock.

In one or more embodiments of the invention, the three-carbon alkylating agent comprises propylene, an oxygenated propyl compound or a mixture thereof. The oxygenated propyl compound comprises isopropyl alcohol, or n-propyl alcohol, or a mixture thereof.

In one or more embodiments of the invention, a portion of said $C_3$ feed stream is produced by a process of reducing an acetone feedstock.

In one or more embodiments of the invention, said process of reducing an acetone feedstock comprises the steps:

(a) supplying an acetone feedstock comprising acetone; and (b) reacting said acetone feedstock with a reducing agent under reduction conditions to produce a reduction effluent having an acetone concentration of at least 0.1 wt. %, and no more than 10 wt. %.

DETAILED DESCRIPTION OF THE EMBODIMENTS

A process is described for producing cumene by contacting a $C_3$ feed stream and benzene under alkylation conditions effective to produce an alkylation effluent comprising at least 1.0 wt. % of cumene based on the total weight of the alkylation effluent. In one or more embodiments, the $C_3$ feed stream and benzene are contacted in the presence of an alkylation catalyst. A portion of said alkylation effluent and an alkylating feedstock having at least one three-carbon alkylating agent is supplied to a treatment zone under treatment conditions to form a treated feedstock. In one or more embodiments, the treatment zone comprises a sorbent or treatment agent. In the treatment zone, at least a portion of an impurities are removed from said alkylation effluent and three-carbon alkylation agent supplied.

As used herein, the term "$C_3$ feed stream" means a stream which comprises a portion of the treated feedstock, and may additionally comprise at least one alkylating feedstock having at least one three-carbon alkylating agent (defined below).

As used herein, the term "three-carbon alkylating agent" means a compound having 3 carbon atoms, and which comprises, for example, one or more of propylene, or an oxygenated propyl compound (including propane).

As used herein, the term "oxygenated propyl compounds" means compounds which comprise, for example, one or more of acetone, isopropyl alcohol (also known as isopropanol), or n-propyl alcohol.

As used herein, the term "impurities" includes, but is not limited to, compounds having at least one of the following elements: nitrogen, halogens, oxygen, sulfur, arsenic, selenium, tellurium, phosphorus, and Group 1 through Group 12 metals. For the purposes of this disclosure, acetone, and/or isopropanol, and/or n-propyl alcohol are not impurities.

The impurities content as used in this disclosure means the parts-per-million by weight ("wppm") of impurities based on the total weight of the $C_3$ feed stream and aromatic compound (if any) in the treatment zone.

In practice, most commercial $C_3$ alkylating agents (such as the three-carbon alkylating agent) contain significant quantities (up to 10.0 wppm by weight) of impurities, typically nitrogenous impurities, such as organic nitrogen compounds, which can act as poisons to the alkylation catalyst. The present process provides an advantageous method of reducing the level of these impurities in the feed(s) to the alkylation catalyst so as to enhance the useful life of the catalyst. The present process is effective not only with conventional $C_3$ feeds or $C_3$ alkylating agents, such as propylene, but also with polar compounds, such as isopropanol, either alone or in combination with acetone and n-propyl alcohol.

In another embodiment, the $C_3$ feed is the treated feedstock.

In yet another embodiment, the $C_3$ feed comprises at least 50 wt. %, preferably, at least 90 wt. % of the treated feedstock.

In one or more embodiments of the present process, a portion of an alkylation effluent and/or at least one three-carbon alkylating agent are supplied to a treatment zone, optionally in the presence of a sorbent (treatment agent), under treatment conditions effective to selectively remove at least a portion of the impurities to produce a treated $C_3$ feed stream. The treated $C_3$ feed stream is then removed from the treatment zone and passed to one or more alkylation zones, where the treated feedstock is contacted with an aromatic stream comprising benzene, optionally with or in the presence of an alkylation catalyst, under alkylation conditions effective to produce an alkylation effluent. The alkylation effluent comprises the desired cumene, together in some embodiments, with unreacted benzene and/or one or more polyalkylated benzenes, particularly diisopropylbenzene.

In some embodiments, rather than supply the entire alkylation effluent to a fractionation system to separate and recover the desired cumene, an aliquot or portion of the alkylation effluent is initially removed from the alkylation effluent and recycled to the treatment zone. The remainder of alkylation effluent is then fed to the fractionation system to recover the desired cumene. In one or more embodiments, at least 50 wt. % of the alkylation effluent is recycled to the treatment zone.

As used herein, the term "alkylation effluent recycle" is used in its commonly accepted sense to mean a portion of the alkylation effluent, which has not been subjected to fractionation or other operations to alter its composition and so has the same composition as the total effluent.

In one or more embodiments, by supplying a portion of alkylation effluent as alkylation effluent recycle to the treatment zone, the concentration of the $C_3$ feed stream in contact with the sorbent (treatment agent) during the impurity reduction treatment step is reduced. In this way, it is possible to reduce the tendency of the $C_3$ feed stream, particularly with polar compounds, such as acetone and/or isopropanol and/or n-propyl alcohol, and mixtures thereof, to undergo side reactions during removal of the impurities by the sorbent (treatment agent).

In one or more embodiments, the $C_3$ feed stream comprises from about 1 wt. %, or 10 wt. %, or 25 wt. %, or 50 wt. % up to about 75 wt. %, or 100 wt. % of said treated feedstock.

In one or more embodiments, from about 1 wt. %, or 5 wt. %, or 10 wt. %, or 15 wt. %, or 30 wt. % up to about 50 wt. %, or 75 wt. %, or 99 wt. % of said alkylation effluent of step (a) is supplied to said treatment zone.

In one or more embodiments, the amount of the alkylation effluent removed and recycled to the treatment zone is equal to at least 10 wt. %, or at least 20 wt. %, or at least 30 wt. %, up to as much as 50 wt. %, or as much as 75 wt. %, or as much as 90 wt. % of said $C_3$ feed stream supplied to said treatment zone.

In one or more embodiments, a portion of the $C_3$ feed stream is produced by a process of reducing an acetone feedstock which is known in the prior art. See European Patent No. 1069099 B1, and U.S. Pat. Nos. 5,015,786 and 5,017,729 of Mitsui Petrochemical Industries, Ltd. for known acetone reduction processes.

In one or more embodiments, the process of reducing an acetone feedstock comprises the steps of:
(a) supplying an acetone feedstock comprising acetone; and
(b) reacting said acetone feedstock with a reducing agent under reduction conditions to produce a reduction effluent having an acetone concentration of at least 0.1 wt. %, or at least 0.5 wt. %, or at least 1 wt. % to up to no more than 10 wt. %, or no more than 15 wt. %, or no more than 20 wt. %. In one or more embodiments, said reduction effluent comprises a portion of said $C_3$ feed stream or a portion said three-carbon alkylating agent.

In some embodiments, the treatment zone is operated under conditions that minimize reaction of the $C_3$ feed stream, such that the ratio of the total weight amount of said at least one three-carbon alkylating agent in said alkylating feedstock over the total weight amount of said at least one three-carbon alkylating agent in said treated feedstock is greater than 0.98, or greater than 0.99 or greater than 0.995. In some embodiments, the first $C_3$ feed stream comprises at least a portion of the treated feedstock. Such conditions include a temperature of less than 200° C., or less than 125° C., such as from about 20° C. to about 125° C., or from about 30° C. to about 100° C.

In other embodiments, the treatment zone is operated under reactive conditions, such that the ratio of the total weight amount of said at least one three-carbon alkylating agent in said alkylating feedstock over the total weight amount of said at least one three-carbon alkylating agent in said treated feedstock is less than 0.95, or less than 0.98 or less than 0.99. In some embodiments, the first $C_3$ feed stream comprises at least a portion of the treated feedstock. Such conditions include a temperature from about 125° C. to about 350° C., such as from about 125° C. to about 250° C. The sorbent (treatment agent) used in the treatment zone operated under such reactive conditions may be an activated clay.

In one or more embodiments, said treatment conditions are selected such that the total amount of said impurities in said treated feedstock is less than 10%, or less than 15%, or less than 25%, or less than 50%, or less than 99% by weight than the total amount of said impurities in the feedstock to the treatment zone. The treatment zone feedstock is comprised of the portion of said alkylation effluent and said at least one three-carbon alkylating agent.

Suitable sorbents (also referred to as treatment agent) for use in the present process comprise alumina, bentonite clays, activated or acidic clays, and/or acidic molecular sieves, such as zeolite 4A, zeolite 5A, zeolite 13X, zeolite beta, mordenite, faujasite-type zeolites (including, for example, zeolite Y, Ultrastable Y (USY), Dealuminized Y (Deal Y)) and molecular sieves of the MCM-22 family.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference.);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO 97/17290), ITQ-30 (described in International Patent Publication No. WO 2005/118476), MCM-36 (described in U.S. Pat. No. 5,250,277), MCM-49 (described in U.S. Pat. No. 5,236,575), MCM-56 (described in U.S. Pat. No. 5,362,697), and mixtures thereof.

Suitable sorbents for use in the present process comprise one or more of UZM-8 (described in U.S. Pat. No. 6,756,030), or UZM-8HS (described in U.S. Pat. No. 7,713,513).

In one embodiment, where the $C_3$ feed stream comprises an oxygenated propyl compound, the sorbent (treatment agent) comprises a bentonite clay, such as Englehard F-24 or F-25, or an activated clay. In this case, adsorption of the impurities may be conducted without recycle of an aliquot of the alkylation effluent without excessive conversion of the oxygenated propyl compound during the adsorption step.

Desirably, the treatment of the $C_3$ feed stream in the treatment unit described above reduces the level of impurities in the $C_3$ feed stream to less than 0.10 ppm by weight.

After passage through the treatment unit, the mixture of the treated $C_3$ feed stream and the alkylation effluent is fed to one or more alkylation zones separate from the treatment unit and each containing an alkylation catalyst. Suitable alkylation catalysts for the present process comprise at least one molecular sieve selected from the group comprising ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, faujasite-type zeolites (including, for example, zeolite Y, Ultrastable Y (USY), Dealuminized Y (Deal Y)), mordenite, and MCM-22 family material (including, but not limited to, MCM-22, PSH-3, SSZ-25, ERB-1, ITQ-1, ITQ-2, ITQ-30, MCM-36, MCM-49, MCM-56 and mixtures thereof).

Other suitable alkylation catalysts for the present process comprise one or more of UZM-8HS or UZM-8.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia, or mixtures of these and other oxides. The latter may be either naturally occurring or in the form of gelatinous precipitates or gels including mixtures of silica and metal oxides. Clays may also be included with the oxide type binders to modify the mechanical properties of the catalyst, or to assist in its manufacture. Use of a material in conjunction with the molecular sieve, i.e., combined therewith or present during its synthesis, which itself is catalytically active, may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

In one embodiment, alkylation is conducted under conditions comprising a temperature of 20° C. to 350° C., a pressure of 100 kPa to 20,000 kPa, and a molar ratio of benzene to $C_3$ feed supplied to said alkylation zone 0.1:1 to 100:1. Desirably, the alkylation conditions are selected so that at least part of said benzene is in the liquid phase.

Where the $C_3$ feed stream comprises an oxygenated propyl compound, the alkylation may be conducted in the presence hydrogen, either added directly to the $C_3$ feed stream to the alkylation zone or is present in the alkylation recycle. Thus, it is found that hydrogen assists in removing the water coproduced with cumene in the alkylation step from the liquid phase reaction medium, thereby reducing the contact between the catalyst and the water and hence, any tendency for the water to deactivate the catalyst. For some catalysts, the presence of hydrogen during the alkylation stage also reduces the deactivation caused by coke formation on the catalyst. Excessive hydrogen should, however, be avoided since it can lead to undesirable loss of benzene to cyclohexane. Conveniently, the molar ratio of hydrogen to oxygenated propyl compound in the $C_3$ feed stream is about 0:1 to about 100:1, such as about 0:1 to about 10:1.

The alkylation step may be carried out batchwise or on a continuous basis. Moreover, the reaction may be carried out in a fixed or moving bed reactor. Fixed bed operation is, however, preferred, typically with the alkylation reaction zone comprising one or a plurality of series-connected beds of alkylation catalysts.

The alkylation step is generally operated so as to achieve substantially complete conversion of the $C_3$ feed stream and hence, the effluent from the alkylation reactor is composed mainly of cumene, unreacted benzene, coproduced water, and other reaction products. In embodiments when the $C_3$ feed stream contains an oxygenate, such as an oxygenated propyl compound, a water co-product is produced. In one or more embodiments, such co-produced water may be removed.

The invention will now be more particularly described with reference to the accompanying drawings.

Figure 1:
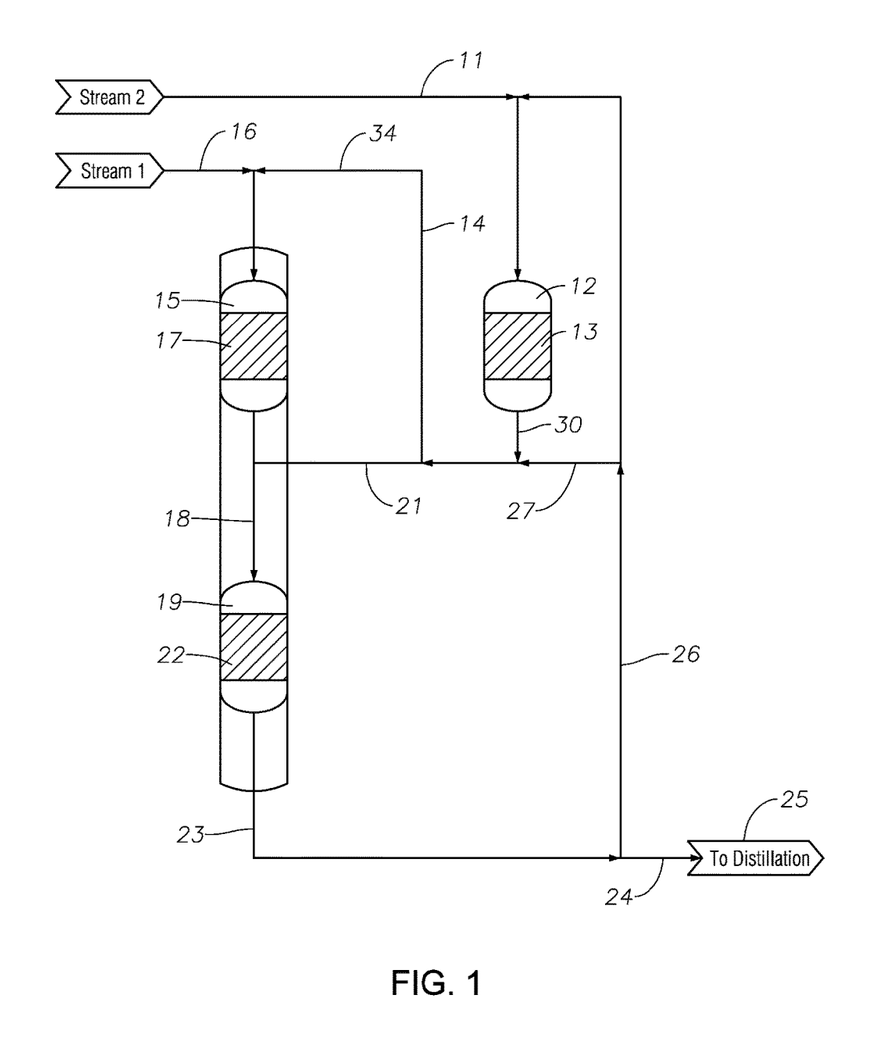
FIG. 1 is a flow diagram of a process for producing cumene according to a first embodiment of the present invention.

FIG. 1 illustrates a process for producing cumene according to a first embodiment of the invention in which a $C_3$ feed stream is supplied by line 11 to an treatment unit 12 containing a sorbent (treatment agent) 13 capable of removing impurities, including, but not limited to, organic nitrogen compounds from the $C_3$ feed stream. Treatment unit 12 is separate from the alkylation reactors 15 and 19. In one embodiment, the $C_3$ feed stream comprises an oxygenated propyl compound and impurities. In another embodiment, the $C_3$ feed stream comprises propylene, an oxygenated propyl compound and impurities. In one or more embodiments, the oxygenated propyl compound comprises acetone, and may further comprise isopropanol, n-propyl alcohol, or a mixture of one or more thereof. After passage through the treatment unit 12, the treated $C_3$ feed stream is in treatment zone effluent line 30.

A portion of the treated feedstock from the treatment zone (treatment zone effluent) may be optionally cooled in one or more heat exchangers (not shown in FIG. 1.) In one or more embodiments, the cooled portion of said treatment zone effluent line 14 may be recycled and supplied to treatment unit 12. In one or more embodiments, an amount of the cooled portion of said treatment zone effluent in line 14 may be fed to the first alkylation reactor 15 via line 34. First alkylation reactor 15 is also supplied by aromatic stream 16 which comprises benzene 16. The first alkylation reactor 15 houses a molecular sieve catalyst 17 and is operated under conditions such that the treated $C_3$ feed stream reacts with the benzene supplied by line 16 to produce a first alkylation effluent. The first alkylation effluent contains cumene and unreacted benzene, but generally no unreacted $C_3$ alkylating agent, and is fed by line 18 to a second alkylation reactor 19 connected in series with the first alkylation reactor 15. In one or more embodiments, an amount of the cooled portion of said treatment zone effluent in line 21 may be fed to the second alkylation reactor 19 via line 18. The second alkylation reactor 19 houses a molecular sieve catalyst 22 and is operated under conditions such that the $C_3$ feed stream reacts with the unreacted benzene in the first alkylation effluent to produce a second alkylation effluent. The second alkylation effluent exits the reactor 19 by way of line 23 and is split wherein a portion is alkylation effluent recycle with the remaining portion of alkylation effluent supplied by line 24 to a distillation train 25 for recovery of the cumene product.

The alkylation effluent recycle is supplied as recycle by line 26 to the treatment unit 12. In one or more embodiments, the alkylation effluent recycle may be optionally cooled in heat exchangers (not shown in FIG. 1) before being supplied to the treatment unit 12.

In one or more embodiments, a portion of alkylation effluent recycle in line 26 is removed via line 27 and mixed with absorption zone effluent to form a mixed stream. The mixed stream is supplied to the first alkylation reactor 15 via line 14, or to the second alkylation reactor 19 via line 21 and line 18.

Generally, the ratio of the weight of the alkylation effluent recycle supplied to the treatment unit 12 to the weight of the remaining portion alkylation effluent sent to the distillation train 25 is greater than 1:1, such as from 10:1 to 20:1.

Figure 2:
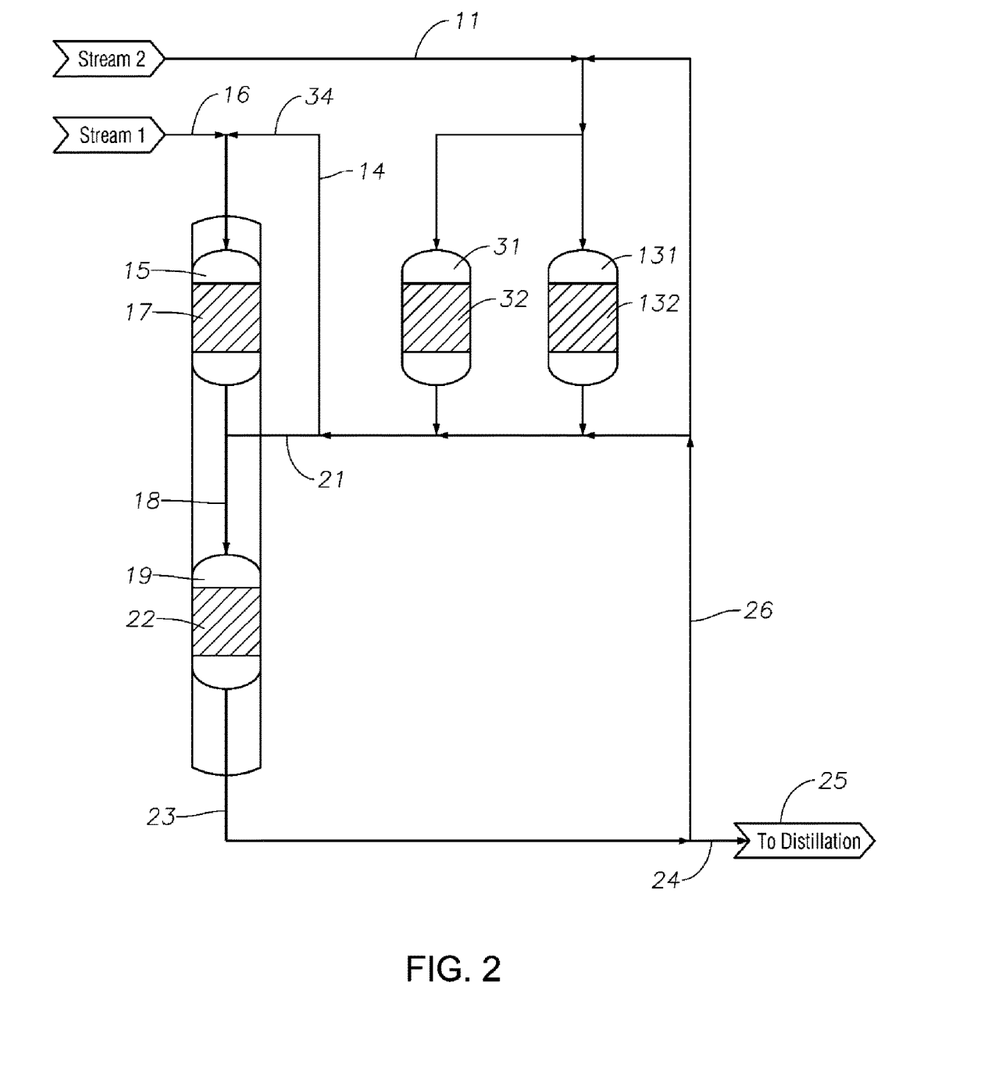
FIG. 2 is a flow diagram of a process for producing cumene according to a second embodiment of the present invention.

A second embodiment of the invention is illustrated in FIG. 2 in which a second treatment unit 131 containing a sorbent (treatment agent) 132 is connected in parallel with the first treatment unit 31 containing sorbent 32. Sorbent 132 may be the same or different from sorbent 32 (treatment agent). The $C_3$ feed stream is fed to one or more treatment units via line 11. As shown in FIG. 2, a portion of the $C_3$ feed stream and alkylation effluent recycle supplied can be diverted to the second treatment unit 131 rather than the first treatment unit 31, thereby allowing replacement of sorbent 32 in the first treatment unit 31 without interruption of impurity removal. After replacement of sorbent 32, the first treatment unit 31 may be returned to service. Alternatively, the $C_3$ feed and alkylation effluent recycle supplied can be diverted to the first treatment unit 31 rather than the second treatment unit 131, to allow replacement of sorbent 132.

The invention is described in the numbered paragraphs as follows.

Paragraph 1. A process for producing cumene comprising the steps of:

(a) contacting a $C_3$ feed stream with an aromatic stream comprising benzene in the presence of an alkylation catalyst under alkylation conditions effective to produce an alkylation effluent comprising at least 1.0 wt. % of cumene based on the total weight of the alkylation effluent;

(b) supplying a portion of said alkylation effluent and at least one three-carbon alkylating agent to a treatment zone under treatment conditions to form a treated feedstock; and wherein said $C_3$ feed stream comprises at least a portion of said treated feedstock.

Paragraph 2. The process of Paragraph 1, wherein said alkylation catalyst comprising at least one of ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Dealuminized Y (Deal Y), mordenite, MCM-22 family material, UZM-8HS, UZM-8, and mixtures thereof.

Paragraph 3. The process of Paragraphs 1 or 2, wherein said treatment zone comprises a treatment agent.

Paragraph 4. The process of Paragraph 3, wherein said treatment agent comprises at least one of alumina, clay, and a molecular sieve.

Paragraph 5. The process of Paragraph 4, wherein said clay comprises one or more of a bentonite clay, an activated clay, or an acidic clay.

Paragraph 6. The process of Paragraph 4, wherein said molecular sieve comprises at least one of zeolite 4A, zeolite 5A, zeolite 13X, zeolite beta, mordenite, a faujasite-type zeolite, MCM-22 family material, UZM-8, UZM-8HS, and mixtures thereof.

Paragraph 7. The process of Paragraph 2 or 6, wherein said MCM-22 family material is selected from the group consisting of MCM-22, PSH-3, SSZ-25, ERB-1, ITQ-1, ITQ-2, ITQ-30, MCM-36, MCM-49, and MCM-56.

Paragraph 8. The process of any one of the preceding Paragraphs, wherein said three-carbon alkylating agent comprises one or more of propylene or an oxygenated propyl compound.

Paragraph 9. The process of Paragraph 8, wherein said oxygenated propyl compound comprises one or more of isopropyl alcohol or n-propyl alcohol.

Paragraph 10. The process of any one of the preceding Paragraphs, wherein from about 1 wt. % up to about 99 wt. % of said alkylation effluent of step (a) is supplied to said treatment zone in step (b).

Paragraph 11. The process of any one of the preceding Paragraphs, wherein said treatment conditions in step (b) are selected such that the ratio of the total weight amount of said at least one three-carbon alkylating agent in said alkylating feedstock over the total weight amount of said at least one three-carbon alkylating agent in said treated feedstock is greater than 0.99.

Paragraph 12. The process of Paragraph 11, wherein said treatment conditions include a temperature less than 200° C.

Paragraph 13. The process of any one of Paragraphs 1 to 10, wherein said treatment conditions in step (b) are selected such that the ratio of the total weight amount of said at least one three-carbon alkylating agent in said alkylating feedstock over the total weight amount of said at least one three-carbon alkylating agent in said treated feedstock is less than 0.99.

Paragraph 14. The process of Paragraph 13, wherein said treatment conditions include a temperature in the range of 125° C. to 350° C.

Paragraph 15. The process of any one of the preceding Paragraphs, wherein said treated feedstock comprises from about 1 wt. % to about 99 wt. % of said $C_3$ feed stream in step (a).

The following non-limiting Examples are provided to further illustrate the present process.

Example 1

A series of experiments was performed in each of which a vial containing one of the adsorbent listed in Tables 1 and 2 was saturated with acetone or isopropanol at room temperature (about 77° C. The supernatant liquid was then sampled after 15 minutes, 1 hour, and 24 hours and its composition measured. The results are summarized in Tables 1 and 2.

TABLE 1

| | Acetone 15 min | | Acetone 1 Hr. | | Acetone 24 Hr. | |
|---|---|---|---|---|---|---|
| Adsorbent Material | Gas Production? | Additional Hydrocarbons Produced? | Gas Production? | Additional Hydrocarbons Produced? | Gas Production? | Additional Hydrocarbons Produced? |
| Molecular Sieve 13X | Visible gas Solution, clear | No | No Gas - clear | Yes | No Gas - clear | Yes |

TABLE 1-continued

|  | Acetone 15 min | | Acetone 1 Hr. | | Acetone 24 Hr. | |
|---|---|---|---|---|---|---|
| Adsorbent Material | Gas Production? | Additional Hydrocarbons Produced? | Gas Production? | Additional Hydrocarbons Produced? | Gas Production? | Additional Hydrocarbons Produced? |
| Molecular Sieve 5A | Visible gas - Solution, cloudy | Yes | No Gas - Clears upon standing | Yes | No Gas - Clears upon standing | Yes |
| Molecular Sieve 4A | No gas Solution, clear | Yes | No Gas - clear | Yes | No Gas - clear | Yes |
| Englehard F-24 | No gas - Solution, cloudy | No | No Gas - Clears upon standing | No | No Gas - Clears upon standing | No |
| Selexsorb CD | Visible gas Solution, clear | No | No Gas - clear | Yes | No Gas - clear | Yes |

Englehard F-24 clay was shown to be the most unreactive material with acetone in that no gas was liberated and that no additional hydrocarbons were produced. Other materials were also unreactive after 15 minutes, but not after 1 hour. Indeed after 24 hrs, Engelhard F-24 clay was still unreactive. These results show that the reaction rate of acetone with Engelhard F-24 clay must be very small.

TABLE 2

|  | 2-propanol 15 min | | 2-propanol 1 Hr. | | 2-propanol 24 Hr. | |
|---|---|---|---|---|---|---|
| Adsorbent Material | Gas Production? | Additional Hydrocarbons Produced? | Gas Production? | Additional Hydrocarbons Produced? | Gas Production? | Additional Hydrocarbons Produced? |
| Molecular Sieve 13X | Visible gas Solution, clear | No | No Gas - Clear | No | No Gas - Clear | No |
| Molecular Sieve 5A | Trace gas - Solution cloudy clears upon standing | No | No Gas - Clears upon standing | No | No Gas - Clears upon standing | No |
| Molecular Sieve 4A | Visible gas Solution, clear | No | No Gas - Clear | No | No Gas - Clear | No |
| Englehard F-24 | Trace gas - Solution cloudy, clears upon standing | No | No Gas - Clears upon standing | No | No Gas - Clears upon standing | No |
| Selexsorb CD | Visible gas Solution clear | No | No Gas - clear | No | No Gas - clear | No |

All of the materials tested are shown to be reactive initially for producing gas, but not for the production of additional hydrocarbons. However, the gas production abates and no additional hydrocarbons are produced. After 1 hour and continuing to 24 hours, all of the materials appear stable to the reaction of 2-propanol.

Example 2

A further series of experiments, similar to those of Example 1, were conducted using Englehard F-24 as the adsorbent, but now a contaminant in the form of an amine compound was added to the acetone or isopropanol. The supernatant liquid was then sampled to determine how much of the contaminant was removed by the adsorbent and the results are summarized in Table 3.

TABLE 3

| Wt % contaminant as measured by GC | 4-Formylmorpholine in acetone | 4-Formylmorpholine in 2-propanol | Pyridine in acetone | Pyridine in 2-propanol |
|---|---|---|---|---|
| Starting mixture | 2.57 | 2.17 | 2.54 | 1.85 |
| After extraction | 1.65 | 1.80 | 1.06 | 1.34 |
| % material removed | 35.8 | 17.1 | 58.3 | 27.6 |

Table 3 shows that clay was very effective at removing two contaminants (poisons) in either 2-propanol (IPA) or acetone, with the removal being more effective in acetone than isopropyl alcohol. This is unexpected since acetone is generally considered to be more polar than 2-propanol.

When numerical lower limits and numerical upper limits are listed herein, ranges from any lower limit to any upper limit are contemplated. All references, patents and documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of,", "selected from the group of consisting of," or "is" preceding the recitation of the composition, element, or elements and vice versa.

The invention claimed is:

1. A process for producing cumene comprising the steps of:
   (a) contacting a $C_3$ feed stream with an aromatic stream comprising benzene in the presence of an alkylation catalyst under alkylation conditions effective to produce an alkylation effluent comprising at least 1.0 wt. % of cumene based on the total weight of said alkylation effluent, wherein said $C_3$ feed stream comprises at least a portion of a treated feedstock;
   (b) supplying from about 1 wt. % up to about 99 wt. % of said alkylation effluent and an alkylating feedstock having at least one three-carbon alkylating agent in the presence of a treatment agent to a treatment zone under treatment conditions to remove at least a portion of the impurities from said alkylation effluent and said alkylating agent to form said treated feedstock, wherein said three-carbon alkylating agent comprises one or more of propylene or an oxygenated propyl compound, said oxygenated propyl compound comprises one or more of isopropyl alcohol or n-propyl alcohol.

2. The process of claim 1, wherein said treatment agent comprises at least one of alumina, clay, and a molecular sieve.

3. The process of claim 1, wherein said alkylation catalyst comprising at least one of ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Dealuminized Y (Deal Y), mordenite, MCM-22 family material, UZM-8HS, UZM-8, and mixtures thereof.

4. The process of claim 2, wherein said clay comprises one or more of a bentonite clay, an activated clay, or an acidic clay.

5. The process of claim 2, wherein said molecular sieve comprises at least one of zeolite 4A, zeolite 5A, zeolite 13X, zeolite beta, mordenite, a faujasite-type zeolite, MCM-22 family material, UZM-8, UZM-8HS, and mixtures thereof.

6. The process of claim 3, wherein said MCM-22 family material is selected from the group consisting of MCM-22, PSH-3, SSZ-25, ERB-1, ITQ-1, ITQ-2, ITQ-30, MCM-36, MCM-49, and MCM-56.

7. The process of claim 1, wherein said treatment conditions in step (b) are selected such that the ratio of the total weight amount of said at least one three-carbon alkylating agent supplied in step (b) over the total weight amount of said at least one three-carbon alkylating agent in said treated feedstock is greater than 0.99.

8. The process of claim 7, wherein said treatment conditions include a temperature less than 200° C.

9. The process of claim 1, wherein said treatment conditions in step (b) are selected such that the ratio of the total weight amount of said at least one three-carbon alkylating agent in said alkylating feedstock over the total weight amount of said at least one three-carbon alkylating agent in said treated feedstock is less than 0.99.

10. The process of claim 9, wherein said treatment conditions include a temperature in the range of 125° C. to 350° C.

11. The process of claim 1, wherein said treated feedstock comprises from about 1 wt. % to about 99 wt. % of said $C_3$ feed stream in step (a).

12. The process of claim 1, wherein said treatment conditions are selected such that the total amount of said impurities in said treated feedstock is less than 50% of the total amount of said impurities in said alkylating feedstock.

13. The process of claim 1, further comprising the step of cooling a portion of said alkylation effluent of step (b).

14. The process of claim 1, further comprising the steps:
   (c) cooling said treated feedstock of step (b); and
   (d) supplying said cooled, treated feedstock to step (a).

15. The process of claim 1, wherein a portion of said $C_3$ feed stream is produced by a process of reducing an acetone feedstock.

16. The process of claim 15, wherein said process of reducing an acetone feedstock comprises the steps:
   (a) supplying an acetone feedstock comprising acetone; and
   (b) reacting said acetone feedstock with a reducing agent under reduction conditions to produce a reduction effluent having an acetone concentration of at least 0.1 wt. % and no more than 10 wt. %.

17. The process of claim 16, wherein said reduction effluent comprises a portion of said $C_3$ feed stream or a portion of said three-carbon alkylating agent.

* * * * *